United States Patent [19]

Theodoropulos et al.

[11] Patent Number: 5,432,285
[45] Date of Patent: Jul. 11, 1995

[54] CHROMOGENIC SUBSTRATE TO PEROXIDASE ENZYMES

[76] Inventors: Spyros Theodoropulos, 2964 Hickory St., Yorktown Heights, N.Y. 10598; Natalie S. Rudolph, 231 Maple Ave., Shrewsbury, Mass. 01545; James E. Woiszwillo, 7 Bradford Rd., Milford, Mass. 01757

[21] Appl. No.: 68,757

[22] Filed: May 28, 1993

Related U.S. Application Data

[60] Division of Ser. No. 925,224, Aug. 3, 1992, Pat. No. 5,215,890, which is a continuation of Ser. No. 778,747, Oct. 18, 1991, abandoned, which is a continuation of Ser. No. 266,948, Nov. 3, 1988, abandoned.

[51] Int. Cl.⁶ .......................................... C07D 417/12
[52] U.S. Cl. ...................................... 546/270; 548/161
[58] Field of Search .......................... 546/270; 548/161

[56] References Cited

U.S. PATENT DOCUMENTS 2,883,389  4/1959  Jucker et al. ..................... 546/244

FOREIGN PATENT DOCUMENTS 927947  5/1963  United Kingdom .

OTHER PUBLICATIONS

Chemical Abstracts vol. 76, Index Guide p. 1281, 1331, 1972.
CA 84(9):59288n Akiba et al. 1975.
CA 84(9):59287m Akiba et al. 1975.
CA 83(21):177580d Akiba et al. 1975.
Akiba, et al. Bull. Chem. Soc. Jpn. 48, 1975, pp. 3270–3273, p. 3262.
Akiba et al. Chem. Lett, 1975 347–350.
Akiba et al. CA 78:111192u, 1973.
Elslager et al. J. Med. Chem. 7, 1964 pp. 493, 496.

*Primary Examiner*—Jane T. Fan
*Attorney, Agent, or Firm*—William R. Moran

[57] ABSTRACT

A novel chromogenic substrate to peroxidase enzymes is provided which is comprised of a mixture of an adduct formed from a hydrozone and a dienophile, and an aromatic nucleophile. The mixture undergos an oxidative coupling in the presence of peroxidase enzymes and peroxides forming a purple indamine dye. The mixture is also stable and unaffected by oxygen of the air or by hydrogen peroxide.

3 Claims, No Drawings

CHROMOGENIC SUBSTRATE TO PEROXIDASE ENZYMES

This is a division, of application Ser. No. 07/925,224, filed Aug. 3, 1992, now U.S. Pat. No. 5,215,890, which in turn is a continuation of application Ser. No. 07/778,747, filed Oct. 18, 1991, now abandoned, which is a continuation of application Ser. No. 07/266,948, filed Nov. 3, 1988, now abandoned, all of which applications are incorporated herein by reference.

FIELD OF THE INVENTION

This invention relates, in general, to a unique chromogenic substrate to peroxidase enzymes. In one aspect, this invention is directed to a chromogenic substrate comprised of an adduct of 3-methyl-2-benzothiazolinone hydrazone and a dienophile capable of undergoing a Michael-type addition, and a nucleophile such as 2-hydroxy-2,4,6-cycloheptatrienone, phenol, naphthol, 3-dimethylaminobenzoic acid and the like, which in the presence of peroxidase enzyme and hydrogen peroxide is oxidized to give an indamine dye. In another aspect, this invention relates to a process for the preparation and use of the chromogenic substrate in a variety of qualitative and quantitative determinations of peroxidases in biological substances. The invention also is directed to the determination of biological components through peroxidase activity. Furthermore, the chromogenic substrate of the present invention also exhibits excellent photochemical stability against ultraviolet light thus simplifying its commercial application.

BACKGROUND OF THE INVENTION

A variety of chromogenic substrates to peroxidase have been reported in the literature as being useful analytical techniques for the detection and measurement of peroxidase activity. Analytical techniques utilizing peroxidase or peroxidase coupled to antibodies and other molecules serve in the measurement of biological properties and components of compounds of interest. Typical components include among others glucose, maltose, bacteria, viruses, enzymes, drugs, hormones and the like, for example, it is known that chromogenic substrates such as benzidine, O-tolidine, O-toluidine, and compounds such as 3-methyl-2-benzothiazolinone hydrazone and 3-(dimethylamino)benzoic acid can be used to monitor peroxidase activity. However, certain of these compounds have been shown to be carcinogenic and very sensitive to light, oxygen from the air and hydrogen peroxide.

In an article by T. T. Ngo and H. M. Lenhoff, Analytical Biochemistry, 105, 389-397 (1980), a chromogenic assay for peroxidase and peroxidase-coupled reactions is disclosed and it is indicated that the assay is sensitive and versatile. This assay is based on the oxidative coupling of 3-methyl-2-benzothiazolinone hydrazone and 3-(dimethylamino)benzoic acid. In the presence of hydrogen peroxide and the aforementioned two compounds, peroxidase catalyzes the formation of a deep purple compound, most likely an indamine dye, which has a broad absorption band between 575 and 600 nm with a peak at 590 nm. Using this assay system solutions of peroxidase can be determined in picomolar amounts by either a rate or a fixed-time method.

In the Journal of Immunological Methods, 60, 61-68 (1983) W. D. Geoghegan et al reported the use of the above Ngo-Lenhoff peroxidase assay for solid phase ELISA. While acknowledging the extreme sensitivity of the method and the rapid production of the indamine dye from the chromogen, the authors indicated that problems were encountered in the adaption of the assay to ELISA, for example, the blank developed color, exposure to light resulted in increased dye production, and other problems. However, by the use of various buffer systems, citric acid, and the like, it was possible for the authors to utilize the Ngo-Lenhoff assay for solid phase ELISA.

Notwithstanding the sensitivity and versatility of the Ngo-Lenhoff method, a chromogenic substrate would be desirable which could exhibit excellent stability against ultraviolet light, and which would not be affected by either hydrogen peroxide or peroxidase alone. It was observed that the presence of hydrogen peroxide alone was detrimental to the Ngo-Lenhoff assay. Additionally, known immunodiagnostic systems usually require that the reaction be terminated by the addition of acid or other chemicals.

Accordingly, one or more of the following objects will be achieved by the practice of the present invention. It is an object of this invention to provide a chromgenic substrate which is useful in the quantitative and qualitative determination of peroxidase in biological substances, particularly biological fluids. A still further object of the present invention is to provide a unique chromogenic substrate to peroxidase which forms upon oxidative interaction a dye which can easily be observed by the naked eye, or determined qualitatively or quantitatively by absorption. Another object of this invention is to provide a substrate to peroxidase which exhibits superior stability against untraviolet light, oxygen of the air, and hydrogen peroxide. A still further object of this invention is to provide a method for detecting peroxidase activity in biological samples or immunodiagnostic formats involving peroxidases by employing the substrate of the present invention. Another object is to provide substrates which can be used in immunodiagnostic systems without the need to terminate the reaction by the addition of acids or other chemicals. These and other objects will readily become apparent to those skilled in the art in the light of the teachings herein set forth.

SUMMARY OF THE INVENTION

The present invention relates to a novel chromogenic substrate to peroxidase, a process for its preparation, and its use in determining peroxidase in biological substances.

The chromogenic substrate is comprised of a colorless mixture of a hydrazone of formula I, a dienophile of the general formula II capable of undergoing a Michael-type condensation with I to form III:

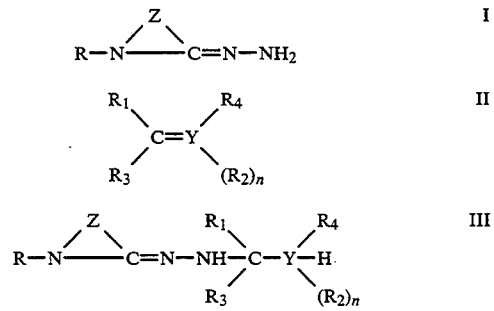

and an aromatic nucleophile IV.

When a mixture of III and an aromatic nucleophile IV such as, 2-hydroxy-2,4,6-cycloheptatrienone interacts with peroxidase enzymes in the presence of peroxides, an oxidative coupling occurs between III and IV forming a purple to blue indamine dye V which can easily be determined quantitatively or quantitatively:

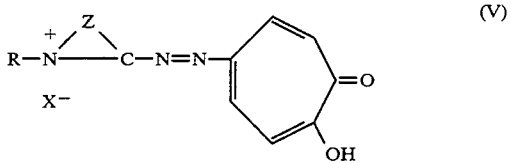
(V)

wherein R, $R_1$-$R_4$, Z, Y, X and n are as hereinafter indicated. By utilizing the above mixture, the developed dye serves as an indicator allowing a qualitative or quantitative determination of peroxidase.

DETAILED DESCRIPTION OF THE INVENTION

As indicated above, the chromogenic substrate to peroxidase enzymes is prepared by the reaction of a hydrazone of formula I and a dienophile of the formula II capable of forming an adduct III of the indicated formula:

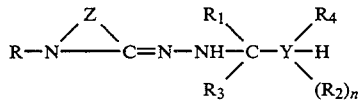
III wherein:

R represents a group containing from 1 to 25, and more preferably, 1 to 12 carbon atoms and includes an alkyl group, e.g., methyl, ethyl, n-propyl, isobutyl, n-amyl, isoamyl, and the like; an alkenyl group. e.g., allyl, methallyl, and the like; an aralkyl group, e.g., benzyl, phenethyl and the like; an alkoxyalkyl group, e.g., methoxyethyl, ethoxyethyl, and the like; an aryloxyalkyl group, e.g., phenoxymethyl, phenoxyethyl, and the like; a hydroxyalkyl group, e.g., hydroxymethyl, hydroxyethyl, beta-hydroxypropyl, and the like; a carboxyalkyl group, e.g., carboxymethyl, carboxyethyl, carboxypropyl, and the like; a carboalkoxyalkyl group, e.g., carbomethoxymethyl, carbomethoxyethyl, carboethoxyethyl, acetoxyethyl, acetoxypropyl, and the like; an arylthioalkyl group, e.g., phenylmercaptomethyl, phenylmercaptoethyl, and the like; a sulfoalkyl-group, e.g., sulfo acid butyl, and the like;

$R_1$ and $R_3$ represent hydrogen, alkyl, aryl, heteroaryl, alkoxycarbonyl, amino, alkylamino, dialkylamino, arylamino, heteroarylamino, containing 1 to 18 carbon atoms;

$R_2$ and $R_4$ represent hydrogen, or alkyl, aryl, heteroaryl, carboxyl, alkoxycarbonyl, alkylcarbonyl, arycarbonyl, amino, alkylamino, dialkylamino, arylamino, heteroarylamino, sulfo, alkylsulfonyl, arylsulfonyl, vinyl sulfonyl, containing 1 to 18 carbon atoms;

and wherein R1 and R4 can together with the atoms to which they are attached, form a cyclic or bicyclic 5 or 6 membered ring which can contain one or more heteroatoms of the group of O, S and N, and can contain a carbonyl or a thiocarbonyl group;

Y represents methylene or nitrogen;

Z represents a group containing non-metallic atoms necessary to complete a heterocyclic or heterobicyclic ring with the atoms to which it is attached. Preferably, Z contains carbon, oxygen or sulfur and up to a total of 25 and more preferably, up to 18 carbon atoms. Z can also be substituted with one or more substituents selected from the group consisting of lower alkyl, nitro, halogen, carboxyl sulfonyl, amino and diamino groups; and n has a value of 1 when Y is carbon and 0 when Y is nitrogen.

The term "heteroaryl" as used throughout the specification and appended claims is meant to include groups such as, pyridyl, quinolyl, benzothiazolyl, benzoxasolyl, indolyl, pyrrolidyl, and the like.

Illustrative heterocyclic groups containing Z include benzothiazole, naphthothiazole, benzoxazole, naphthoxazole, benzoselenazole, indoline, or heterocyclic groups of the quinoline or pyridine series.

Typical examples of the dienophiles are methylvinyl ketone, phenylvinylsulfone, methylvinylsulfone, an imine, maleic acid, diethylmaleate, maleimide, N-phenylmaleimide, and the like.

The aromatic nucleophiles are mono-cyclic or polycyclic aryl or heteroaryl compounds containing up to about 24 and perferably up to about 18 carbon atoms, and are sustituted with one or more hydroxyl or amino groups, or a combination of hydroxy and amino groups. Accordingly, the nucleophiles include classes of compounds such as the phenols, naphthols, anilines, aminonaphthalenes, aminonaphthols, pyridines, quinolines, diazoles, oxazoles, thiazoles, and the like, which contain at least one amino or hydroxy group and can contain additional amino or hydroxy groups. Preferred aromatic nucleophiles of formula IV include compounds such as, phenols, naphthols, 3-dimethylaminobenzoic acid, dimethylaminonaphthalene sulfonic acid, aminonaphthalenes, 2-hydroxy-2,4,6-cycloheptatrienone, and the like.

The adduct III is mixed with an aromatic nucleophile IV in a buffer to form a colorless mixture.

In a preferred embodiment of the present invention, the chromogenic substrate is formed from a mixture of 3-methyl-2-benzothiazolinone hydrazone adduct to 2-amino-2-thiazoline VI and to 2-pyridinecarboxaldehyde-4-nitrophenylhydrozone VII, and a neucleophile:

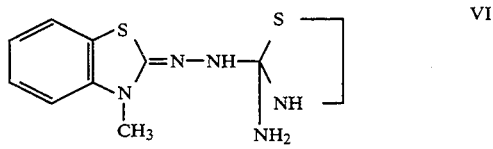
VI

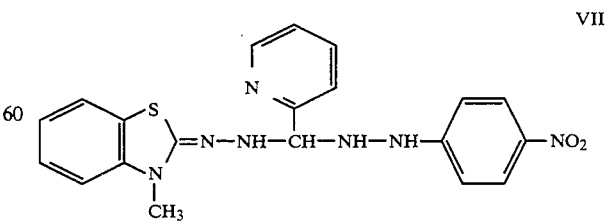
VII

These compounds undergo an oxidative coupling in the presence of peroxidase enzymes and peroxides to form an indamine dye having the general formula VIII:

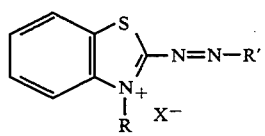

wherein R' represents an aromatic nucleophile as defined above, and X represents an anion selected from the group consisting of F, Cl, Br, I, Acetate, phthalate, phosphate, citrate, borate, sulfate, and nitrate. The developed dye serves as an indicator allowing a qualitative or quantitative determination of peroxidases in biological fluids and other immunodiagnostic formates.

In another preferred embodiment, a mixture of a hydrazone and 2-amino-2-thiazoline-4-carboxylic acid are utilized.

In some instances, it is not necessary to isolate the adduct since it can be directly formed in the buffer solution and reacted with the aromatic nucleophile. For example, structure VI need not be isolated, whereas structure VII is isolated.

In general, a biological sample containing peroxidase enzymes such as, for example, horseradish peroxidase, develops a yellow, red or blue color when a mixture of III and an aromatic nucleophile, and hydrogen peroxide is added. The yellow to blue color which develops upon the oxidative interaction is due to formation of an indamine dye. When the nucleophile is 2-hydroxy-2,4,6-cycloheptatrienone the indamine dye has the structural formula VIII. A mixture of VI and a nucleophile in buffer solution is stable against ultraviolet light, oxygen and remains unchanged when hydrogen peroxide is added. Only upon addition of the peroxidase, does the colored dye develop, thus revealing the presence of peroxidase activity.

The buffers constituting the solutions of III and aromatic nucleophiles, among others, are phosphate, citrate, saline, borate, phthalate or combination of more than one with the preferred buffer being citric acid-dibasic sodium phosphate, pH 7.0 buffer.

The chromogenic substrates to peroxidase of the present invention are useful in a wide variety of areas, as a biochemical tool for the detection and measurement of peroxidase activity in biological samples and in the detection and measurements of biological components. For example, the chromogenic substrates of the present invention due to their stability against light, and oxygen of the air can be employed in immunodiagnostic assays involving pairs of antibodies, one bound to a solid phase and the other labeled with peroxidase to permit detection.

The substrate of the present invention is also useful in systems involving labeled avidin/strepavidin and biotinylated antibodies employed in histochemistry and other diagnostic formats. As previously indicated, the chromogenic substrates of this invention are ideal agents due to their photochemical stability and their stability against oxygen of the air and hydrogen peroxide. The novel compounds of the present invention are accordingly intended for use in a variey of applications where peroxidases are involved. The following examples illustrate the best mode presently contemplated for the practice of this invention.

EXAMPLE 1

PREPARATION OF 3-METHYL-2-BENZOTHIAZOLINONE HYDRAZONE (MBTH) ADDUCT TO 2-PYRIDINECARBOXALDEHYDE 4-NITROPHENYL-HYDRAZONE (PCNPH)

300 milligrams of PCNPH and 215 milligrams of MBTH hydrochloride were mixed in 10 ml of sodium acetate-citric acid buffer, pH 5 to 5.2 (prepared by dissolving 27.2 grams of sodium acetate trihydrate in 2 liters of deionized water and titrated with 0.1 Molar citric acid to pH 5 to 5.2) and the mixture allowed to stir at ambient temperature for 24 hours. The yellow precipitate was filtered and washed with water.

EXAMPLE 2

PREPARATION OF MBTH ADDUCT TO 2-AMINO-2-THIAZOLINE 150 milligrams of MBTH hydrochloride mixed with 2 grams of 2-amino-2-thiazoline hydrochloride in one liter of 0.1 Molar citrate-acetate buffer (prepared as in Example 1 above) containing 0.5 grams of urea hydrogen peroxide. The solution was used in immunoassays.

EXAMPLE 3

PREPARATION OF BUFFER SOLUTION OF 8-ANILINO-NAPHTHALENE SULFONIC ACID (ANS)

3.2 g of ANS-sodium salt was dissolved in one liter of 0.1 Molar citrate-acetate buffer pH 5.0 prepared according to Example 1. The solution was used in immunoassays.

EXAMPLE 4

PREPARATION OF BUFFER SOLUTION OF 4-CHLORO-1-NAPHTHOL 450 milligrams of 4-chloro-1-naphthol dissolved in 250 milliliters of 1:1 glycerol: methanol(v:v) was mixed with 750 milligrams of 2,2'-azino-bis(3-ethylbenzo-thiazoline-6-sulfonic acid)-diammonium salt dissolved in 750 milliliter of 0.1 Molar citrate-acetate buffer pH 5.0 prepared according to Example 1.

EXAMPLE 5

PREPARATION OF 2-HYDROXY-2,4,6-CYCLOHEPTA-TRIENONE BUFFER SOLUTION 1.0 gram of 2-hydroxy-2,4,6-cycloheptatrienone was dissolved in glycerol:methanol, (v:v). To this was then added 900 milliliters of 0.1 M citrate-acetate buffer pH 5.0 to make 1 liter of the 2-hydroxy-2,4,6-cycloheptatrienone buffer solution.

EXAMPLE 6

PREPARATION OF CHROMOGEN SUBSTRATE SOLUTION

A mixture containing one part of MBTH adduct buffer solution of Example 2 and one part of a solution of the nucleophile described in Example 3, 4, or 5 constitutes the final preparation of the chromogenic substrate to be used in immunoassays.

EXAMPLE 7

HCG-IMMUNOASSAY

Reagents to perform a sandwich immunoassay for HCG were obtained from commercial supply companies. To HCG antibody bound to a membrane device was added positive HCG control (Ventrex HCG 20 MIN). HCG antibody labeled with horseradish peroxidase was then added and allowed to incubate for 10–15 minutes at ambient temperature. The membrane was then washed with PBS buffer (phosphate buffered saline, see Example 11) pH 7.5 to remove unbound material. To the membrane was then added 3 drops of chromogenic substrate (prepared by mixing equal parts of solution of Example 2 and solution of Example 3) and incubated at ambient temperature for 1–5 minutes. The membrane was washed with PBS leaving a permanent blue color.

EXAMPLE 8

HCG-IMMUNOASSAY

Reagents to perform a sandwich immunoassay for HCG were obtained from a commercial source. To HCG antibody bound to a membrane device was added positive HCG control (Ventrex HCG 20 MIN). HCG antibody labeled with horseradish peroxidase was also added and allowed to incubate for 10–15 minutes at ambient temperature. The membrane was then washed with distilled water to remove unbound material. To the membrane was then added 3 drops of chromogenic substrate (prepared by mixing equal parts of solution of Example 2 and solution of Example 5) and incubated at ambient temperature for 1–5 minutes. The membrane was washed with distilled water leaving a permanent purple color.

EXAMPLE 9

IMMUNOHISTOLOGICAL ASSAY

Tissue slides were prepared as usual. Sections were cleaved in xylene and dehydrated through graded alcohols. Tissue was incubated with hydrogen peroxide for 10 minutes to block endogenous peroxidase and washed with PBS pH 7.5 buffer (Example 11), containing 1% horse serum. Incubation of tissue with primary antibody for 30 minutes was followed and washed with PBS containing 1% horse serum and 0.05% Tween 20. Incubation with avidin-horseradish peroxide conjugate for 15 minutes was followed and tissue washed with PBS containing 0.05% Tween 20. After the avidin-HRP incubation and subsequent wash, slides were incubated for 5 minutes in citrate-acetate buffer (0.1 M sodium acetate adjusted to pH 5 with 0.1 M citric acid). Tissue was stained for ten minutes with chromogenic substrate prepared by mixing equal parts of solution of Example 2 and solution of Example 3, and counterstained for 5–10 minutes with Nuclear Fast Red/Alum (see Example 10) and rinsed in water until clear. The chromogen substrate forms a dark blue ring-like precipitate around positive cells. No precipitate forms on negative controls, that is, tissues incubated in the first step with nonreactive or nonimmune antiserum or ascites.

EXAMPLE 10

PREPARATION OF NUCLEAR FAST RED/ALUM

Nuclear Fast Red/Alum was prepared by boiling 0.4% Nuclear Fast Red in 100 ml 5% aqueous aluminum potassium sulfate until dissolved, cooling and filtering, giving a clear solution.

EXAMPLE 11

PREPARATION OF PBS BUFFER

PBS pH 7.5 buffer was prepared by mixing 8.0 grams of NaCl, 0.2 grams KCl, 1.15 grams $Na_2HPO_4$ and 0.2 grams $KH_2PO_4$ in 1 liter distilled water.

Although the invention has been illustrated by the preceding examples, it is not to be construed as being limited to the materials disclosed therein, but rather, the invention encompasses the generic area as hereinbefore disclosed. Various modifications and embodiments can be made without departing from the spirit or scope thereof.

What is claimed is:

1. A hydrazone compound of the formula:

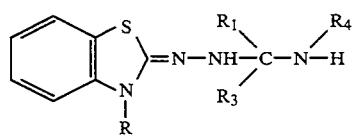

wherein:
R contains from 1 to 12 carbon atoms and is selected from the group consisting of alkyl, alkenyl, aralkyl, alkoxyalkyl, aryloxyalkyl, hydroxyalkyl, carboxyalkyl, carboalkoxyalkyl, arylthioalkyl, sulfoalkyl;
$R_1$ and $R_3$ represent hydrogen, or alkyl, aryl, pyridyl, alkoxycarbonyl, amino, alkylamino, and dialkylamino containing 1 to 18 carbon atoms;
$R_4$ represent hydrogen, or alkyl, aryl, carboxyl, alkoxycarbonyl, alkylcarbonyl, arylcarbonyl, amino, alkylamino, dialkylamino, arylamino, sulfo, alkylsulfonyl, arylsulfonyl, vinyl sulfonyl, and p-nitrophenylamino, containing 1 to 18 carbon atoms;
or $R_1$ and $R_4$ together form a 5 or 6 membered ring which can contain a carbonyl, a thiocarbonyl group, or a sulfur atom.

2. The hydrazone compound having the formula:

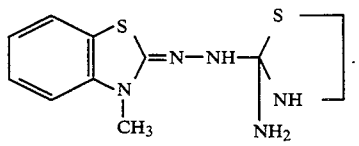

3. The hydrazone compound having the formula:

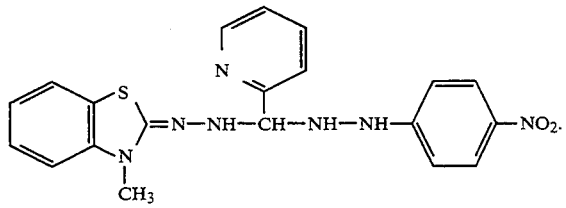

* * * * *